United States Patent [19]

Matsuda et al.

[11] Patent Number: 4,994,542
[45] Date of Patent: Feb. 19, 1991

[54] SURGICAL ADHESIVE

[75] Inventors: Takehisa Matsuda, Minoo; Teruo Takakura, Yokohama; Tetsuo Itoh, Shiga, all of Japan

[73] Assignees: Asahi Glass Co., Ltd., Tokyo; Sanyo Chemical Industries, Ltd., Kyoto, both of Japan

[21] Appl. No.: 320,054

[22] Filed: Mar. 7, 1989

[30] Foreign Application Priority Data

Mar. 7, 1988 [JP] Japan ................................ 63-52918

[51] Int. Cl.$^5$ ............................................. C08G 18/38
[52] U.S. Cl. .................................... 528/70; 528/904
[58] Field of Search .................................. 528/70, 904

[56] References Cited

U.S. PATENT DOCUMENTS 4,359,558 11/1982 Gould et al. .......................... 528/75
4,403,083 9/1983 Marans et al. ...................... 528/904
4,412,054 10/1983 Yamabe et al. ........................ 528/70
4,740,534 9/1984 Matsuda et al. .................... 523/111

FOREIGN PATENT DOCUMENTS 64-2101 1/1989 Japan .

Primary Examiner—Maurice J. Welsh
Attorney, Agent, or Firm—Oblon, Spivak, McClelland, Maier & Neustadt

[57] ABSTRACT

Elastomeric or flexible surgical adhesives, comprising (i) a NCO-terminated hydrophilic urethane prepolymer derived from a fluorine-containing polyisocyanate and a hydrophilic polyether polyol of higher oxyethylene content, or a combinatioin of (i) with (ii) an unsaturated cyano compound containing a cyano group directly bonded to a polymerizable double bond, exhibit low toxicity, may be safely used for bonding of tissues and possess a rapid cure rate and sufficient bonding power.

20 Claims, No Drawings

SURGICAL ADHESIVE

BACKGROUND OF THE INVENTION

1. Field of the Invention:

The present invention relates to surgical adhesives.

2. Description of the Background:

U.S. Pat. No. 4,740,534 discloses surgical adhesives, which contain NCO-terminated (i.e., containing terminal NCO groups) hydrophilic urethane prepolymers derived from organic polyisocyanates, such as tolylene diisocyanates (TDI) and diphenylmethane diisocyanates (MDI), and hydrophilic polyether polyols of higher oxyethylene content, or combinations thereof with unsaturated cyano compounds containing a cyano group directly bonded to a polymerizable double bond.

Such adhesives, however, in which aromatic polyisocyanates, such as TDI and MDI are used as the starting materials, exhibit toxicity problems, because their hydrolysis products, tolylene diamine and diaminodiphenylmethane, possess a high activity in a microbial mutagenicity test (Ames test). On the other hand, aliphatic or cycloaliphatic polyisocyanates, such as hexamethylene diisocyanate, are of low reactivity and catalysts such as heavy metal compounds and amines are required when these compounds are used as surgical adhesives, and the use of such catalysts causes problems in regard to toxicity.

Thus, there remains a need for surgical adhesives which do not give rise to mutagenic hydrolysis products and do not require the use of toxic catalysts.

SUMMARY OF THE INVENTION

Accordingly, one object of the present invention is to provide novel surgical adhesives of lower toxicity.

It is another object of the present invention to provide adhesives for surgery having improved curability.

It is still another object of the present invention to provide surgical adhesives which possess sufficient bonding power for tissues.

Briefly, these and other objects of the present invention which will become more readily apparent during the following detailed description, have been achieved by a surgical adhesive, which comprises (i) a NCO-terminated hydrophilic urethane prepolymer derived from a fluorine-containing polyisocyanate and a hydrophilic polyether polyol of higher oxyethylene content, or a combination of (i) with (ii) an unsaturated cyano compound containing a cyano group directly bonded to a polymerizable double bond.

DETAILED DESCRIPTION OF THE PREFERRED EMBODIMENTS

The NCO-terminated hydrophilic urethane prepolymer (i), used in the surgical adhesive of the present invention, can be derived from (a) at least one organic polyisocyanate comprising a fluorine-containing polyisocyanate and (b) at least one hydrophilic polyether polyol with or without (c) one or more other polyols.

Suitable fluorine-containing (F-containing) polyisocyanates, used in producing NCO-terminated hydrophilic urethane prepolymer (i) according to the present invention, include, F-containing aliphatic polyisocyanates, and F-containing cycloaliphatic polyisocyanates, and mixtures of two or more of them.

Suitable F-containing aliphatic polyisocyanates include, for example, F-containing diisocyanates, represented by the formulae (1) and (2):

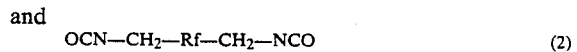

In the formulae (1) and (2), Rf is a perfluoroalkylene group containing suitably 1 to 20, preferably 1 to 10 carbon atoms, and 0 to 10, preferably 0 to 4 ether linkages. Specific examples include $-(CF_2)_m-$, $-CF_2CF_2OCF_2CF_2-$, $-CF_2CF_2O(CF_2)_mOCF_2CF_2-$, $-CF(CF_3)O(CF_2)_mOCF(CF_3)-$, and $-CF_2CF_2OCF_2CF(CF_3)O(CF_2)_mOCF(CF_3)CF_2OCF_2CF_2-$, wherein n is an integer of 1 to 20, preferably 1 to 10, and m is an integer of 1 to 5, preferably 1 to 2. Among these, preferred are $-(CF_2)_m-$. F-containing polyisocyanates can be produced according to the methods described in *J. Macromol. Sci.-Phys.*, Bl, 831 (1967) and Japanese Laid-Open Pat. No. 108055/1982.

Illustrative examples of F-containing cycloaliphatic polyisocyanates are fluorinated cycloaliphatic polyisocyanates, containing 4 to 15 carbon atoms (not including those in the NCO groups), such as F-containing isophorone diisocyanates, fluorinated hydrogenated xylylene diisocyanates, fluorinated hydrogenated 4,4′-diphenylmethane diisocyanates and fluorinated trans-cyclohexane-1,4-diisocyanates.

Among these polyisocyanates, preferred are F-containing aliphatic polyisocyanates, particularly F-containing diisocyanates of the formula (2). The most preferred is 2,2,3,3,4,4,5,5-octafluorohexamethylene diisocyanate (hereinafter referred to as FHDI).

In the present adhesives, the F-containing polyisocyanates may be used alone or in combination with other polyisocyanates. Suitable examples of such other polyisocyanates include aromatic polyisocyanates containing 6 to 20 carbon atoms, not including the carbon atoms in the NCO groups, such as o-, m- and p-phenylene diisocyanates (hereinafter referred to as PDI), 2,4- and 2,6-tolylene diisocyanates (TDI), diphenylmethane-2,4′-and 4,4′-diisocyanates (MDI), naphthalene-1,5-diisocyanate, triphenylmethane-4,4′,4″-triisocyanate, polymethylene polyphenylenepoly-isocyanates (PAPI) obtained by phosgenation of anilineformldehyde condensation products, m- and p isocyanatophenyl sulfonyl isocyanate, and the like; aliphatic polyisocyanates containing 2 to 18 carbon atoms, such as ethylenediisocyanate, tetramethylenediisocyanate, hexamethylenediisocyanate (hereinafter referred to as HDI), dodecamethylenediisocyanate, 1,6,11-undecane diisocyanate, 2,2,4-trimethylhexanediisocyanate, lysine diisocyanate, 2,6-diisocyanato-methyl caproate, bis(2-isocyanatoethyl fumarate, bis(2-isocyanatoethyl) carbonate, 2-isocyanatoethyl-2,6-diisocyanato hexanoate, and the like; alicyclic polyisocyanates containing 4 to 15 carbon atoms, such as isophorone diisocyanate, dicyclohexylmethane diisocyanates, cyclohexylene diisocyanates, methylcyclohexylene diisocyanates, bis(2-isocyanatoethyl)-4-cyclohexene-1,2-dicarboxylate, and the like; araliphatic polyisocyanates containing 8 to 15 carbon atoms, such as xylylene diisocyanates, diethylbenzene diisocyanates, and the like; and modified polyisocyanates of these polyisocyanates, containing urethane, carbodiimide, allophanate, urea, biuret, urethdione, urethimine, isocyanurate and/or oxazolidone groups, such as urethane-modified TDI, carbodiimide-modified MDI, urethane-modified MDI, and the like; as well as mixtures of two or more of them. Among these polyisocyanates, preferred are aromatic polyisocyanates (preferably diisocyanates), particularly PDI, TDI (including the 2,4- and 2,6-isomers, mixtures of them and crude TDI), MDI (including the 4,4'- and 2,4'-isomers, mixtures of them and crude MDI or PAPI), and modified polyisocyanates containing urethane, carbodiimide, allophanate, urea, biuret and/or isocyanurate groups, derived from PDI, TDI and/or MDI. The most preferred is p-PDI, in the interest of low toxicity.

These other polyisocyanates may be used in an amount of suitably 80% or less, preferably 50% or less, more preferably 20% or less, based on the total weight of the polyisocyanates.

Illustrative of suitable hydrophilic polyether polyols (b) are adducts of ethylene oxide (hereinafter referred to as EO) or combinations thereof with other alkylene oxide(s) (hereinafter referred to as AO) to one or more compounds containing at least two active hydrogen atoms, such as polyhydric alcohols, polyhydric phenols, amines, polycarboxylic acids, phosphorous acids and the like. Suitable examples of polyhydric alcohols include dihydric alcohols, such as ethylene glycol, propylene glycol, 1,3- and 1,4-butanediols, 1,6-hexanediol, neopentyl glycol, diethylene glycol, bis(hydroxymethyl)cyclohexane, bis(hydroxyethyl)benzene, hydrogenated bisphenol A, hydrogenated bisphenol F, polytetramethylene glycols, polyester diols and silanol-terminated polysiloxanes; trihydric alcohols, such as glycerol, trimethylol propane, trimethylol ethane, 1,2,3-butane triol, 1,2,6-hexane triol and polyester triols; and polyhydric alcohols having 4 to 8 or more hydroxyl groups, such as pentaerythritol, diglycerol, $\alpha$-methylglucoside, sorbitol, xylitol, mannitol, glucose, fructose, sucrose, and the like. Exemplary of suitable polyhydric phenols are mono- and polynuclear phenols, such as hydroquinone, catechol, resorcin, pyrogallol, and bisphenols (bisphenol A, bisphenol F, bisphenol S, and the like), as well as phenol-formaldehyde condensation products. Suitable amines include ammonia; alkanol amines, such as mono-, di- and tri-ethanol amines, isopropanol amines and the like; aliphatic, aromatic, araliphatic and alicyclic monoamines, such as $C_1$ to $C_{20}$ alkyl amines (methyl-, ethyl-, isopropyl-, butyl-, octyl-, and laurylamines, and the like), aniline, toluidine, naphthylamines, benzylamine, cyclohexylamine and the like, aliphatic, aromatic, alicyclic and araliphatic polyamines, such as $C_2$ to $C_6$ alkylene diamines (such as ethylene diamines), diethylene triamine, tolylene diamines, phenylene diamines, xylylene diamines, methylene dianilines, diphenylether diamines, isophorone diamine, cyclohexylene diamines, dicyclohexylmethane diamines and the like; and heterocyclic polyamines, such as piperazine, N-aminoethyl-piperazine, and other heterocyclic polyamines, disclosed in Japanese Patent Publication 21044/1980.

Suitable AO, which may be employed in combination with EO for producing polyether polyols, include, for example, propylene oxide (hereinafter referred to as PO), 1,2-, 2,3-, 1,3-, and 1,4-butylene oxides, styrene oxide, epichlorohydrin and the like, as well as combinations of two or more of them. Among these, PO is preferred.

The addition of EO or the combination thereof with AO to the active hydrogen atom-containing compounds can be carried out in any conventional manner, with or without catalysts, such as alkaline catalysts, amine catalysts, or acidic catalysts, under normal or elevated pressure, in a single step or in a multi-stage process. The addition of EO and AO may be performed by random-addition, block-addition or a combination thereof, for example random-addition followed by block-addition. Random-addition is preferred.

The hydrophilic polyether polyols have an equivalent weight (molecular weight per hydroxyl group) of suitably 100 to 5,000 daltons, preferably 200 to 3,000 daltons, and an oxyethylene content of suitably at least 30%, preferably 50–90% by weight. Polyether polyols having an equivalent weight higher than 5,000 are too viscous to be used as surgical adhesives, while an equivalent weight of less than 100 results in a lack of the flexibility required for surgical adhesives. Polyether polyols of oxyethylene content less than 30% by weight, having insufficient hydrophilic nature, have a poor reactivity with body fluids resulting in a reduced cure rate and poor bonding power with water-rich tissue. The content of the primary hydroxyl groups of the polyether polyols is preferably at least 30%, more preferably at least 50%, most preferably at least 70%.

Other polyols (c) may be optionally used in conjunction with the hydrophilic polyether polyols, and include low molecular weight polyols and/or hydrophobic polyols. Examples of such polyols are the polyhydric alcohols mentioned above as starting materials for the hydrophilic polyether polyols; AO adducts (such as PO adducts) of these polyhydric alcohols or other active hydrogen atom-containing compounds; and polyester polyols. Illustrative examples of polyester polyols are the condensation products of dihydric and/or trihydric alcohols (ethylene glycol, propylene glycol, 1,3- and 1,4-butanediols, 1,6-hexanediol, neopentyl glycol, diethylene glycol, glycerol, trimethylolpropane and the like) and/or polyether polyols (such as those described above) with dicarboxylic acids (aliphatic or aromatic dicarboxylic acids, such as glutaric, adipic, sebacic, fumaric, maleic, phthalic and terephthalic acids) or ester-forming derivatives thereof (anhydrides and lower alkyl esters, such as maleic and phthalic anhydrides, dimethyl terephthalate, and the like); and ring-opening polymerization products of lactones, such as $\epsilon$-caprolactone. Among these polyols (c), polyether polyols are preferred over polyester polyols.

The whole polyols, (b) and optionally (c), used for producing the NCO-terminated urethane prepolymer, have an oxyethylene content suitably of at least 30%, preferably 50–90% by weight, an average equivalent weight of suitably 100–5,000 daltons, preferably 200–3,000 daltons, and suitably 2 to 8 hydroxyl groups (average), preferably 2 to 4 hydroxyl groups.

In reacting at least one polyisocyanate (a) comprising a F-containing polyisocyanate with at least one hydrophilic polyether polyol (b) and optionally one or more other polyols (c) to form NCO-terminated hydrophlic urethane prepolymers, the ratio of NCO/OH is generally 1.5 to 5.0, preferably 1.7 to 3.0. The reaction of (a) with (b) and optionally (c) to form the prepolymer can be performed in any conventional manner. The reaction may be carried out in the presence of a catalyst.

The prepolymers may be prepared by reacting (a) with a mixture of (b) and (c), or by reacting (a) successively in any order with (b) and (c). The prepolymers may be prepared by blending a prepolymer obtained from the reaction of (a) with (b) with a prepolymer obtained from the reaction of (a) with (c), for example, by blending a prepolymer obtained from (b) with a prepolymer obtained from a low molecular weight polyol (equivalent weight 50 to 500) to reduce the viscosity.

In the case where a F-containing polyisocyanate is used in conjunction with one or more other polyisocyanates, these polyisocyanates can be reacted in any order, but it is preferred to react the other polyisocyanates at the early stages of prepolymer production so as to provide F-containing polyisocyanate-terminated prepolymers.

The NCO-content of the present NCO-terminated hydrophilic prepolymers is suitably 1 to 10%, preferably 2 to 8% by weight. Prepolymers with a NCO-content less than 1% by weight exhibit poor reactivity, result in a reduction in cure rate, and possess insufficient bonding power to tissues. A NCO-content higher than 10% by weight results in brittle cured resins of poor flexibility which are not deformable according to the movement of living organism.

Illustrative examples of suitable unsaturated cyano compound (ii) containing a cyano group directly bonded to a polymerizable double bond are cyano(-meth)acrylic acids (cyanoacrylic acid and cyanomethacrylic acid; similar expressions are used hereinafter); cyano(meth)acrylic esters, such as methyl cyano(meth)acrylates, ethyl cyano(meth)acrylates, isobutyl cyano(-meth)acrylates and the like; (meth)acrylonitriles, cyano(meth)acrylonitriles, and the like; and mixtures of two or more of these compounds. Among these, preferred are cyanoacrylic esters, especially methyl cyanoacrylate, ethyl cyanoacrylate and isobutyl cyanoacrylate.

In adhesive compositions comprising said hydrophilic urethane prepolymer (i) and said unsaturated cyano compound (ii), the content of (i) is suitably at least 20%, preferably 50 to 95%, more preferably 70 to 90%, based on the total weight of (i) and (ii). Use of less than 20% of (i) results in poor flexibility and poor bonding ability with living organisms. Combinations of (i) with 10% or more of (ii) provide more rapid cure rates and can be applied for bonding of blood vessels, wherein quick-curing is required. By varying the ratio of (i) to (ii), there can be attained desired hardness in balance with the flexibility required by the movement of living organisms. Adhesives containing higher amounts of (i) are effective for applications requiring flexibility, such as bonding of blood vessels; while adhesives with a lower content of (i), provide relatively higher rigidity and are suitable for bonding of bone or circumference thereof.

The adhesives of this invention may contain, if necessary, physiologically active materials, such as antimicrobials, local anesthetics, antihistamines, antiphlogosis analgestics, antibiotics, astringents, vitamins, antifungal agents, peripheral nervous system anesthetics, vasodilators, hormones, crude drug essences, tinctures, crude drug powders, hypotensive agents, and the like; fillers, for example, carbon black, metal oxides, such as red iron oxide and titanium dioxide, silicates, such as calcium silicates and sodium silicates, acrylic resin powders, various ceramic powders, and the like; softening agents, such as DBP (dibutylphosphate), DOP (dioctylphosphate), TCP (tricresylphosphate), tributoxyethylphosphates, and other esters of various types; and stabilizers, such as trimethyldihydroquinone, phenyl-$\beta$-naphthyl amine, p-isopropoxydiphenylamine, diphenyl-p-phenylene diamine, and the like. These additives may be used in amounts of suitably 0 to 20%, preferably 0 to 5%, based on the weight of the adhesive according to the invention.

Both the NCO-terminated prepolymer(s) and the cyano compound(s) are rapidly polymerized in the presence of trace amounts of water, such as moisture in the air, resulting in the formation of a tough membrane. Accordingly, it is necessary to use dry materials as these main components and any other compounding additives, and it is preferred to exclude air during the production of the adhesives. Adhesives, thus-obtained, can be stored for a long period of time within airtight vessels, such as an ampule.

In applying the adhesives of the present invention in surgery, suitable application methods include those employing brushes, tweezers, applicators, specially-designed spatula or syringes, or the like; and those involving spray coating using inert gases, such as Freons, nitrogen or the like. Bonding of tissues can be achieved, for example, by direct coating techniques, simply applying the adhesive to the tissues; by cover-coating techniques, using, as an aid for hemostasis or anastomosis, thin sheets or meshes made of polyesters (such as Dacron), oxidized cellulose, collagen, polyurethanes or the like, cotton like materials, or fragments of tissues, such as veins, musculation or mascular membrane or the like (wherein these materials are applied onto the affected parts followed by coating thereon the adhesives); or by sealing techniques for sutured parts, wherein sutures are partly applied followed by applying the adhesive to seal the remaining conjugation parts. The adhesives of the invention can be used, not only for tissue adhesion, but also as coating, embolus or sealing materials in cardiovascular surgery via direct coating or injection by catheters. Applicable tissues include, for example, vascular vessels, heart, lung, esophagus, stomach, liver, pancreas, spleen, skin, and the like.

The surgical adhesives according to the present invention, comprising NCO-terminated hydrophilic urethane prepolymer (i) derived from a F-containing polyisocyanate and hydrophilic polyether polyol, have a sufficiently high cure rate and provide sufficient bonding power for tissues, even without any catalyst, in spite of using F-containing polyisocyanates of the aliphatic polyisocyanate type as the starting material; while usual aliphatic polyisocyanates are of low reactivity and require catalysts such as heavy metal compounds and amines, which cause toxicity problems. The surgical adhesives of the present invention cause little or no toxicological problems, since the F-containing polyisocyanates used therein show no mutagenic activity; whereas aromatic polyisocyanates, such as TDI and MDI, generally show a high mutagenic activity and raise the possibility of carcinogenesis during use within tissues for long periods of time. In addition, the surgical adhesives of the present invention are elastomeric or flexible and can be deformed in accordance with the movement of tissues.

The surgical adhesives of the present invention, comprising prepolymer (i) and unsaturated cyano compound (ii), can attain cure accelerating effects throughout their entirety (not only on the tissue contact surface but also inside of the adhesive), shortening of operation period, and an increase in over all bonding power with body tissue, by the synergistic action of rapid polymerization of (ii) in contact with a body fluid (water) along with the reactivity of the NCO groups of (i).

In addition, the adhesives of the present invention can provide sufficient cure rate, bonding power to tissue, and flexibility to permit body movement, required for surgical adhesives, without using any organic solvents, which may cause toxicity problems.

Accordingly, application of the adhesives of the present invention to surgical operations makes it possible to perform operations with the method of adhesion, instead of suturing as in a conventional operation. Thus, there can be attained remarkable improvements in medical technology, such as shortening of operation time, hemostasis, prevention of enzymes leaking from viscera or the like, prevention of minute blood vessel occlusion, and nerve anastomosis, as well as provisional fixing before suturing, and ensuring of bonding by the combination of adhesion with suturing. Furthermore, the present invention can provide high reliability and high efficiency, not only in an operation, but also in medical treatments at large, for example, joining of incised wound or cutting portions, adhesive treatment in dental surgery, curative means by controlled release of drugs in combination with physiologically active materials, and so on.

Having generally described the invention, a more complete understanding can be obtained by reference to certain specific examples, which are included for purposes of illustration only and are not intended to be limiting unless otherwise specified.

EXAMPLES

In the following, parts and % represent parts by weight and % by weight, respectively. Raw materials used in the following examples are as follows:

| | |
|---|---|
| PEO: Polyethyleneoxide, | PPO: Polypropyleneoxide, |
| PEG: polyetheleneglycol, | PPG: Polypropyleneglycol, |
| PTMG: Polytetramethyleneglycol, | ECA: Ethyl cyanoacrylate, |
| FHDI: 2,2,3,3,4,4,5,5-octafluorohexamethylene diisocyanate, | |
| TDI: Tolylene diisocyanate. | |

Preparation of Prepolymers:

NCO-terminated prepolymers A1 to A4, and B1 to B4 were prepared by mixing each polyether polyol, dried under reduced pressure, with each polyisocyanate, and reacting them for 8 hours at 80° C.

Prepolymer A1

A polyether polyol (a EO/PO random copolymer having an average M.W. of 3,000 daltons and an oxyethylene content of 80%) was reacted with FHDI to obtain a NCO-terminated hydrophilic urethane prepolymer having an NCO-content of 2.5%.

Prepolymer A2

A polyether polyol (a EO/PO random copolymer having an average M.W. of 4,000 daltons and an oxyethylene content of 60%) was reacted with FHDI to obtain a NCO-terminated hydrophilic urethane prepolymer having an NCO-content of 3.4%.

Prepolymer A3

A polyether polyol (a mixture of 80 parts of a PEG having an average M.W. of 2,000 daltons and 20 parts of PPG having an average M.W. of 200 daltons) was reacted with FHDI to obtain a NCO-terminated hydrophilic urethane prepolymer having an NCO-content of 6.4%.

Prepolymer A4

A polyether polyol (a PTMG-EO block copolymer having an average M.W. of 2,000 daltons and an oxyethylene content of 50%) was reacted with FHDI to obtain a NCO-terminated hydrophilic urethane prepolymer having an NCO-content of 6.7%.

Prepolymer B1

A polyether polyol (a EO/PO random copolymer having an average M.W. of 3,000 daltons and an oxyethylene content of 80%) was reacted with TDI to obtain a NCO-terminated hydrophilic urethane prepolymer having an NCO-content of 2.5%.

Prepolymer B2

A polyether polyol (a EO/PO random copolymer having an average M.W. of 3,000 daltons and an oxyethylene content of 10%) was reacted with FHDI to obtain a NCO-terminated hydrophobic urethane prepolymer having an NCO-content of 2.5%.

Prepolymer B3

A polyether polyol (a EO/PO random copolymer having an average M.W. of 4,000 daltons and an oxyethylene content of 60%) was reacted with HDI to obtain a NCO-terminated hydrophilic urethane prepolymer having an NCO-content of 3.4%.

Prepolymer B4

A polyether polyol (a mixture of 80 parts of a PEG having an average M.W. of 2,000 daltons and 20 parts of PPG having an average M.W. of 200 daltons) was reacted with MDI to obtain a NCO-terminated hydrophilic urethane prepolymer having an NCO-content of 6.4%.

Preparation of Surgical Adhesives:

Surgical adhesives were prepared as follows:

Examples 1 to 4

Surgical adhesives consisting essentially of prepolymers A1, A2, A3, and A4, respectively were used.

Example 5

A surgical adhesive was obtained by mixing and dehydrating 70 parts of prepolymer A1 with 30 parts of ECA.

Comparative Examples 1 to 4

Surgical adhesives were obtained as in Examples 1 to 4 but substituting prepolymers B1, B2, B3, and B4 for prepolymers A1, A2, A3, and A4, respectively.

Comparative Example 5

A surgical adhesive consisting essentially of ECA was used.

Comparative Example 6

A surgical adhesive was obtained by dissolving 7 parts of a nitrile rubber (nitrile content: 38 to 40%) into 50 parts of dehydrated dry nitromethane, followed by adding thereto with stirring 7 parts of ECA and 1 part of TDI.

Testing of Surgical Adhesives:

A carotid artery of a goat was clamped at about 5 cm of distance and then incised 3 mm along the longitudinal direction, followed by coating a small amount of each adhesive. Within several minutes after application of the adhesive, the clamps were removed. Then, the tissue adhesivity and hemostasis were carefully evaluated. Testing was carried out under heparinized anti-coagulation conditions, in order to exclude the stanching effects of blood coagulation to evaluate effects of the adhesives. The flexibility and bonding strength with tissue were also evaluated. The results are shown in Table 1, according to the following criteria:
o = good
x = poor

Method for Safety Test

The safety of the surgical adhesives was evaluated by microbial mutagenicity test (Ames test). The huydrolyzate (diamine) of the surgical adhesive was used as the testing sample. Salmonella typhimurium and Escherichia coli were used as testing bacteria. Test results are shown in Table 1, according to the following criteria:
− = negative (no mutagenic activity was observed);
+ = positive (mutagenic activity was observed).

Obviously, numerous modifications and variations of the present invention are possible in light of the above teachings. It is therefore to be understood that within the scope of the appended claims, the invention may be practiced otherwise than as specifically described herein.

2. The adhesive of claim 1, wherein said fluorine-containing polyisocyanate is at least one member selected from the group consisting of fluorine-containing aliphatic polyisocyanates and fluorine-containing cycloaliphatic polyisocyanates.

3. The adhesive of claim 1, wherein said fluorine-containing polyisocyanate is at least one member selected from the group consisting of fluorine-containing diisocyanates of the formulas (1) and (2):

wherein Rf is a perfluoroalkylene group containing 1 to 20 carbon atoms and up to 10 ether linkages 4. The adhesive of claim 3, wherein said perfluoroalkylene group is at least one member selected from the group consisting of $-(CF_2)_n-$, $-CF_2CF_2OCF_2-$, $-CF_2O(CF_2)_mOCF_2-$, $-CF(CF_3)O(CF_2)_mOCF(CF_3)-$, and $-CF_2CF_2OCF_2CF(CF_3)O(CF_2)_mOCF(CF_3)CF_2OCF_2CF_2-$, wherein n is an integer of 1 to 20, and m is an integer of 1 to 10.

5. The adhesive of claim 1, wherein said polyisocyanate component comprises 2,2,3,3,4,4,5,5,-octafluorohexamethylene diisocyanate.

6. The adhesive of claim 1, wherein said polyisocyanate component further comprises up to 80% by weight of at least one polyisocyanate selected from the group consisting of aromatic polyisocyanates containing 6 to 20 carbon atoms, aliphatic polyisocyanates containing 2 to 18 carbon atoms, alicyclic polyisocyanates contain-

TABLE 1

| Surgical Adhesive | Cure Time sec. | Flexibility | Bonding Power with Tissue | Safety Test (Ames Test) | Clinical Sign at Adhesive Joints |
|---|---|---|---|---|---|
| Example | | | | | |
| 1 | 20 | O | O | − | Very good adhesivity. No bleeding after declamping. |
| 2 | 21 | O | O | − | Very good adhesivity. No bleeding after declamping. |
| 3 | 15 | O | O | − | Very good adhesivity. No bleeding after declamping. |
| 4 | 28 | O | O | − | Very good adhesivity. No bleeding after declamping. |
| 5 | 5 | O | O | − | Very good adhesivity. No bleeding after declamping. |
| Comparative Example | | | | | |
| 1 | 20 | O | O | + | Good adhesivity. |
| 2 | 400 | O | X | − | Slow curing. Due to premature curing, bleeding from adhesive joints. |
| 3 | >400 | O | X | − | Very slow curing. Due to premature curing, much bleeding from adhesive joints. |
| 4 | 400 | O | X | + | Slow and inhomogeneous curing characteristics. Bleeding from adhesive joints. |
| 5 | 5 | X | X | − | Very fast curing. Delamination immediately after declamping. Massive bleeding. |
| 6 | 350 | O | X | + | Slow curing. Due to premature curing, bleeding after declamping |

What is claimed as new and desired to be secured by letters patent of the U.S. is:

1. A surgical adhesive, which comprises at least one NCO-terminated hydrophilic urethane prepolymer, derived from (a) an organic polyisocyanate component comprising at least one fluorine-containing polyisocyanate and (b) a polyol component comprising at least one hydrophilic polyether polyol having an oxyethylene content of at least 30%.

ing 4 to 15 carbon atoms, araliphatic polyisocyanates containing 8 to 15 carbon atoms, not including carbon atoms in NCO groups, and derivatives thereof containing one or more groups selected from the group consisting of urethane, carbodiimide, allophanate, urea, biuret, urethdione, urethimine, isocyanurate and oxazolidone groups.

7. The adhesive of claim 1, wherein said prepolymer has an isocyanate-content of 1 to 10% by weight.

8. The adhesive of claim 1, wherein said polyol component has an oxyethylene content of at least 30%.

9. The adhesive of claim 1, wherein said polyol component has an average equivalent weight of 100 to 5,000 and an average number of hydroxyl groups of 2 to 8.

10. The adhesive of claim 1, wherein said hydrophilic polyether polyol is at least one adduct of ethylene oxide or a combination thereof with one or more other alkylene oxides with at least one compound containing two or more active hydrogen atoms.

11. The adhesive of claim 10, wherein said compound containing two or more active hydrogen atoms is at least one member selected from the group consisting of polyhydric alcohols, polyhydric phenols, amines, polycarboxylic acids and phosphorous acids.

12. The adhesive of claim 1, wherein said hydrophilic polyether polyol is at least one member selected from the group consisting of polyoxyethylene polyols, polyoxyethylene/oxypropylene polyols and polyoxyethylene/oxybutylene polyols.

13. The adhesive of claim 1, wherein said polyol component further comprises at least one polyol selected from the group consisting of low molecular weight polyols, hydrophobic polyether polyols and polyester polyols.

14. The adhesive of claim 1, wherein said prepolymer is obtained by reacting said polyisocyanate component with said polyol component in such an amount to obtain a NCO/OH ratio of 1.5 to 5.0.

15. The adhesive of claim 1, which further comprises at least one unsaturated cyano compound containing a cyano group directly bonded to a polymerizable double bond.

16. The adhesive of claim 15, which comprises 20 to 90% by weight of said prepolymer and 10 to 80% by weight of said cyano compound.

17. The adhesive of claim 15, wherein said cyano compound is at least one member selected from the group consisting of cyanoacrylic acid, cyanomethacrylic acid, cyanoacrylates, cyanomethacrylates, acrylonitrile, methacrylonitrile, cyanoacrylonitrile, and cyanomethacrylonitrile.

18. The adhesive of claim 15, wherein said cyano compound is at least one member selected from the group consisting of methyl cyanoacrylate, ethyl cyanoacrylate, and iso-butyl cyanoacrylate.

19. The adhesive of claim 1, which further comprises up to 20% by weight of at least one additive selected from the group consisting of carbon black, metal oxides, silicates, acrylic resin powders, ceramic powders, softening agents, stabilizers, and physiologically active materials.

20. The adhesive of claim 19, wherein said physiologically active material is selected from the group consisting of antimicrobials, local anesthetics, antihistamines, antiphlogosis analgestics, antibiotics, astringents, vitamins, antifungal agents, peripheral nervous system anesthetics, vasodilators, hormones, crude drug essences, tinctures, crude drug powders and hypotensive agents.

* * * * *